United States Patent [19]
Barmore et al.

[11] Patent Number: 5,483,819
[45] Date of Patent: Jan. 16, 1996

[54] METHOD OF DETECTING THE PERMEABILITY OF AN OBJECT TO OXYGEN

[75] Inventors: Charles R. Barmore, Moore, S.C.; Christopher Bull, Bethesda, Md.

[73] Assignee: W.R. Grace & Co.-Conn., New York, N.Y.

[21] Appl. No.: 250,085

[22] Filed: May 27, 1994

[51] Int. Cl.$^6$ .................... G01N 21/78; G01N 15/08
[52] U.S. Cl. .................... 73/38; 422/56; 422/80; 436/1; 436/5
[58] Field of Search .................... 73/38; 436/1, 3, 436/5, 904; 422/56, 86

[56] References Cited

U.S. PATENT DOCUMENTS

| | | | |
|---|---|---|---|
| 4,349,509 | 9/1982 | Yoshikawa et al. | 422/57 |
| 4,526,752 | 7/1985 | Perlman et al. | 436/1 |
| 4,657,736 | 4/1987 | Marsoner et al. | 422/56 |
| 4,886,690 | 12/1989 | Davis et al. | 428/36.6 |
| 4,889,731 | 12/1989 | Williams, Jr. | 426/106 |
| 4,956,212 | 9/1990 | Bekele | 428/36.6 |
| 5,107,696 | 4/1992 | Mayer et al. | 73/38 |
| 5,316,949 | 5/1994 | Bull et al. | 436/5 |

FOREIGN PATENT DOCUMENTS

| | | | |
|---|---|---|---|
| 4151554 | 5/1992 | Japan | 436/1 |

*Primary Examiner*—Hezron E. Williams
*Assistant Examiner*—Michael J. Brook
*Attorney, Agent, or Firm*—Valerie E. Looper

[57] ABSTRACT

A device for use in a method of detecting the permeability of an article to oxygen is disclosed. A redox indicator and test object are vacuum sealed between a support and a peelable barrier film.

15 Claims, 5 Drawing Sheets

METHOD OF DETECTING THE PERMEABILITY OF AN OBJECT TO OXYGEN

FIELD OF THE INVENTION

This application relates to a method of detecting the oxygen permeability of an article and various improved ways of implementing that method.

In particular, this application relates to an improved support for an oxygen indicating strip and sample which allows easier sample preparation and greater convenience of use.

BACKGROUND OF THE INVENTION

It is well known that polymeric materials can be formed into thin, transparent films and optionally coated with various substances such as silica. When this is done, however, it is difficult to tell whether the film has been properly made, or whether it has flaws, especially if the film has multiple layers, particularly when a gas barrier layer is present. Many critical flaws are not visible. Hand calibration of thickness is not feasible. For oxygen barrier films, the standard analytical instrument for measuring oxygen permeability, as described in U.S. Pat. No. 5,107,696, can only detect average permeability over an area typically five square inches.

Various methods of measuring the presence of oxygen are known for use in various systems. U.S. Pat. No. 5,316,949, issued May 31, 1994 to Bull et al., which is incorporated by reference, discloses a new method which is easy to set up and use, and provides quick results. Compared to the available technology, this method is less expensive, and yields an order of magnitude increase in sensitivity. Unlike available technology, this method can spatially resolve the permeability of an object, i.e., detect streaks, cracks, pinholes and other features. Also, this method more closely correlates with the real-world use for which it was originally developed, to test a food wrap, since it uses a food simulant and ambient temperature, pressure, humidity and gas mixtures for test conditions.

The present application relates more specifically to a multilayer device which can be made for mounting and evaluating the oxygen transmission rate and pattern for an object. An oxygen indicator strip and the test object can be vacuum packaged in a composite, multilayer, oxygen barrier, peelable film structure. The peelable film structure is made so that at least a portion of one of the oxygen barrier layers can be easily separated from the rest of the film structure. Where the oxygen barrier layer has been removed, an underlying oxygen permeable layer is exposed. Once the oxygen barrier layer has been removed, the test can proceed.

Various types of packaging for oxygen sensitive substances are known. Vacuum packages for fresh red meat having peelable layers are disclosed in U.S. Pat. No. 4,886,690 issued to Davis et al. Dec. 12, 1989. U.S. Pat. No. 4,889,731 issued to Williams Dec. 26, 1989 discloses pull tabs for use with such packages. U.S. Pat. No. 4,956,212 issued to Bekele Sep. 11, 1990 discloses a means of improving the effectiveness of oxygen barrier layers in such vacuum packages. U.S. Pat. No. 5,346,735 issued Sep. 13, 1994 to Logan et al., which is incorporated herein as if set forth in full, discloses a peelable film structure with enhanced oxygen barrier properties. None of these references disclose analytical methods for the permeation of oxygen through the packages.

Although this application is written in terms of a specific end use, one of ordinary skill in the art will readily recognize that it is a general tool for detecting cracks and pinholes wherever oxygen might be used as an indicator. For example, it could be used to detect flaws in sheets of aluminum foil. In that case, oxygen permeability per se might not be the primary interest, if one is interested in the physical integrity of the foil. Similarly, the integrity of opaque or tortuous path type materials such as ceramics could be tested as well.

OBJECTS AND ADVANTAGES OF THE INVENTION

It is, therefore, an object of this invention to provide a method and apparatus for detecting the rate of permeation of oxygen through a barrier at various locations.

Another object is to provide as the detecting component for oxygen analysis a stable sheet comprising a redox compound dissolved in a solvent or dispersed in a carrier, which sheet is supported on a substrate which has good handling properties.

Yet another object of the invention is to provide devices for handling samples which improve the ease and convenience of running the analysis.

This invention offers a number of advantages, including the ease and speed with which a spatial representation of the oxygen permeability of an object can be obtained.

A particular advantage of the present invention is that the use of a multilayer film device for mounting samples makes sample handling easier. Peelable multilayer film devices add to the ease of operation by allowing the fully prepared samples to be stored for extended periods after photoreduction has been performed. This gives the test operator greater control of the sampling and analysis schedule.

DETAILED DESCRIPTION OF THE INVENTION

This invention relates to improved ways of implementing a method of detecting the gas permeability of an object. This application is written in terms of the specific test for which it was developed, that is, a test which yields spatial resolution of an article's permeability to oxygen. However, upon reading this application, one with ordinary skill in the art will readily appreciate that the test devices described herein can be used in a number of different ways, and could be used, for example, as supports for analysis for other gases, or as a means for determining the average permeability of gases through articles.

In order to detect the permeability of an article to oxygen, a redox indicator is dispersed in a carrier, the carrier is placed on a high barrier support (such as glass) and the article is placed on top of the carrier. The carrier is thereby fully enclosed by the test article and the support. A hermetic seal is formed in the area where the test article and the support overlap. The vacuum packaging process removes contaminant oxygen and provides for the formation of a hermetic seal between the test article and the support. Preferably contaminant oxygen is minimized in the article and the carrier, usually by vacuum treatment, i.e., packaging in a flexible bag using vacuum packaging equipment. The indicator is then photoreduced, thereby removing residual oxygen within the carrier. According to this invention, the test article, carrier and support do not need to be removed from a vacuum bag. Instead a composite, multilayer, oxygen barrier, peelable film structure is used, and the oxygen is allowed to permeate through the article and into the carrier. Where the carrier is exposed to oxygen, the redox indicator reacts with the oxygen, and redox changes can be observed as fluorescence upon exposure of the indicator to light. Redox indicators, such as thiazine derivatives, oxazine derivatives and a flavin, or mixtures thereof, are preferred.

Areas of relatively low permeability will be dark, while areas of higher permeability will show a brighter fluorescence. The position of streaks, pinholes and surface artifacts can be resolved to a location within an area of about a square millimeter.

In one embodiment of this invention, a multilayer device with a peelable barrier layer can be made for mounting and evaluating the oxygen transmission rate and pattern of a test object. This device has the advantage of having physical properties that can be controlled nearly at will, thereby facilitating automation of the oxygen transmission test method.

Also, the device tends to preserve the intimate, void-free contact between the article, carrier, and support throughout the testing process.

BRIEF DESCRIPTION OF THE DRAWINGS

FIG. 3 shows one embodiment of a tab arrangement for delaminating or peeling apart the two films comprising the peelable barrier film used in the present invention. FIG. 3 shows the tab to be on the relatively permeable film, but it could also be on the relatively impermeable film.

Figure 1:
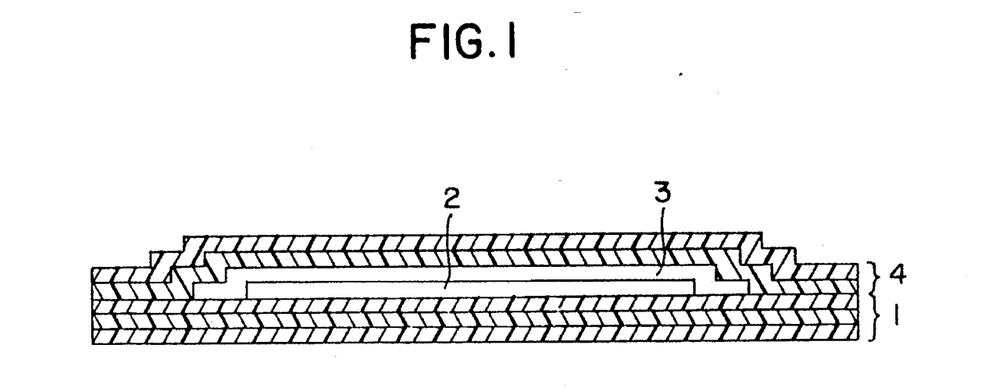
FIG. 1 is a cross section which represents one embodiment of the present invention.

In a preferred embodiment, the device has multiple layers with a variety of functions. A diagram of the device is shown in FIG. 1. A support structure (1) is preferably a thermoplastic film with physical properties adapted to make the oxygen permeability analysis easier to handle. Adjacent to support structure (1) are the indicator (2) and the test object (3). The indicator (2) and the test object (3) are smaller in area than the support structure (1). A multilayer peelable barrier (4) covers the indicator (2) and the test object (3) and contacts the support structure (1) around their perimeter. The support structure (1) and the multilayer peelable barrier (4) are sealable where they come in contact with one another.

Figure 2:
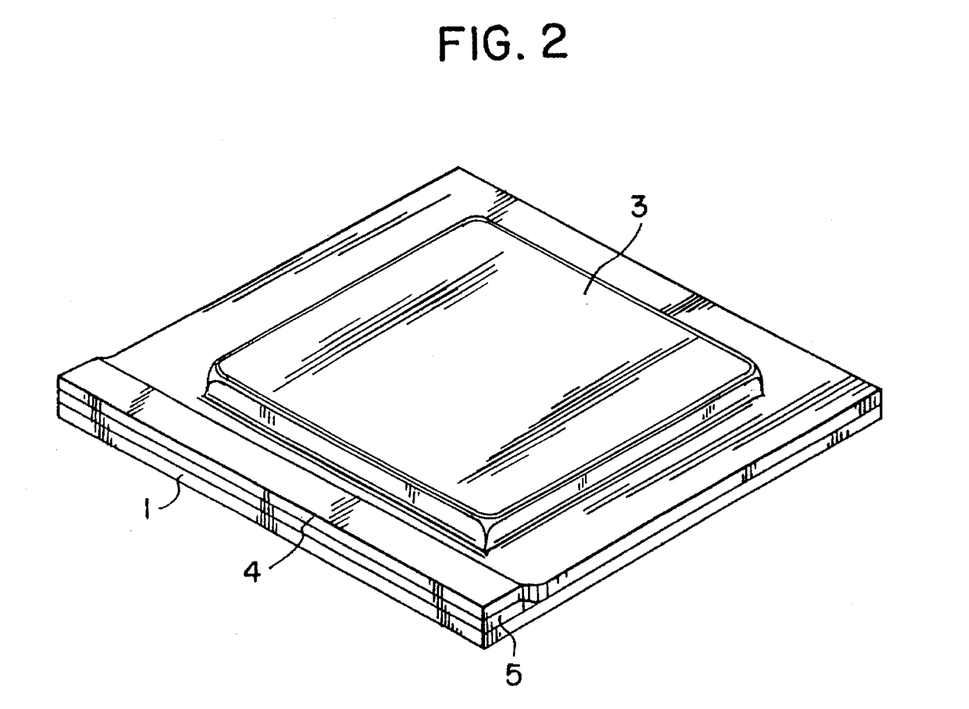
FIG. 2 is a perspective view of one embodiment of the present invention.

FIG. 2 shows another view of the device, including tab 5, which is added for ease in removing a portion of multilayer peelable barrier (4) from the device. Peelable barrier (4) covers the test object (3) and is sealed around the perimeter of the test object so that it assumes the shape of the test object.

Figure 3:
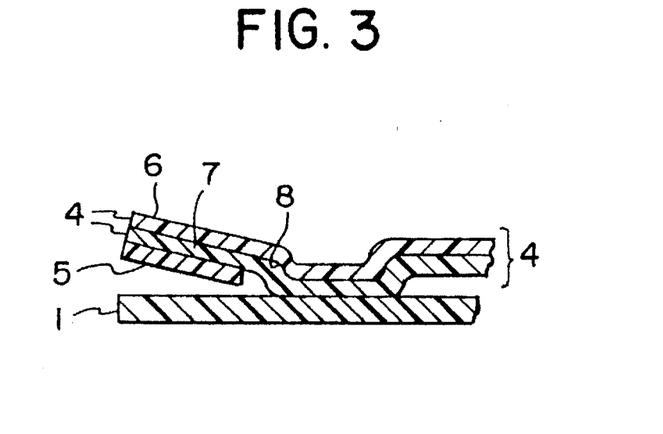
Figure 4:
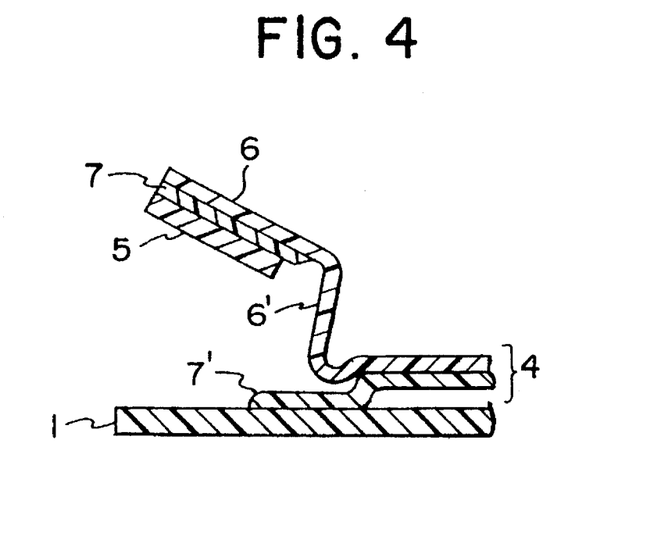
FIG. 4 shows the peeling process underway in the film of FIG. 3. Rupture of a portion of the permeable film has taken place.
Figure 5:
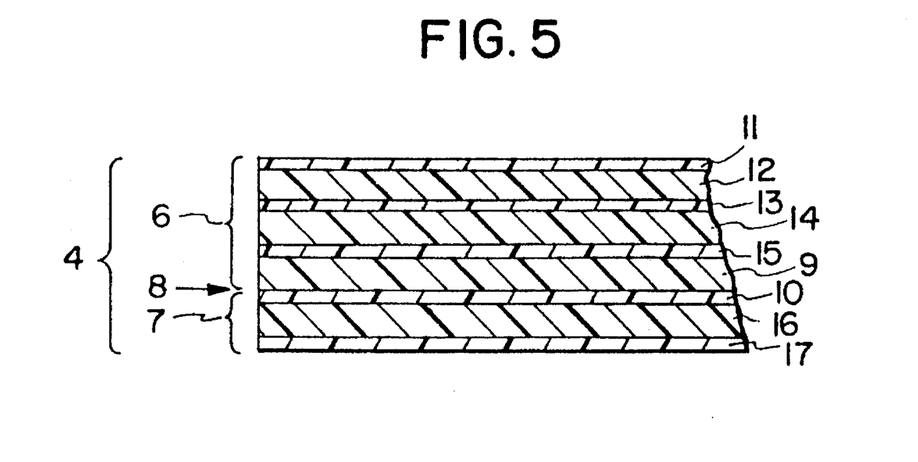
FIG. 5 is a detail of the peelable film.

The peelable barrier (4) is preferably a composite film and is shown in greater detail in FIGS. 3 and 4. The two films (6) and (7) which make up the peelable barrier (4) are shown bonded at interface (8). Film (6) is a relatively impermeable or high gas barrier film, while film (7) is relatively permeable. FIG. 5 shows that films (6) and (7) can be multilayer structures which are preferably coextruded together to form what appears to be a single, multilayer barrier film (4). Film (6) has inner layer (9) and film (7) has inner layer (10) which do not readily adhere to each other, and form a relatively weak bond at interface (8). Other layers (11–17) are shown merely to illustrate a multilayer film structure.

Figure 6:
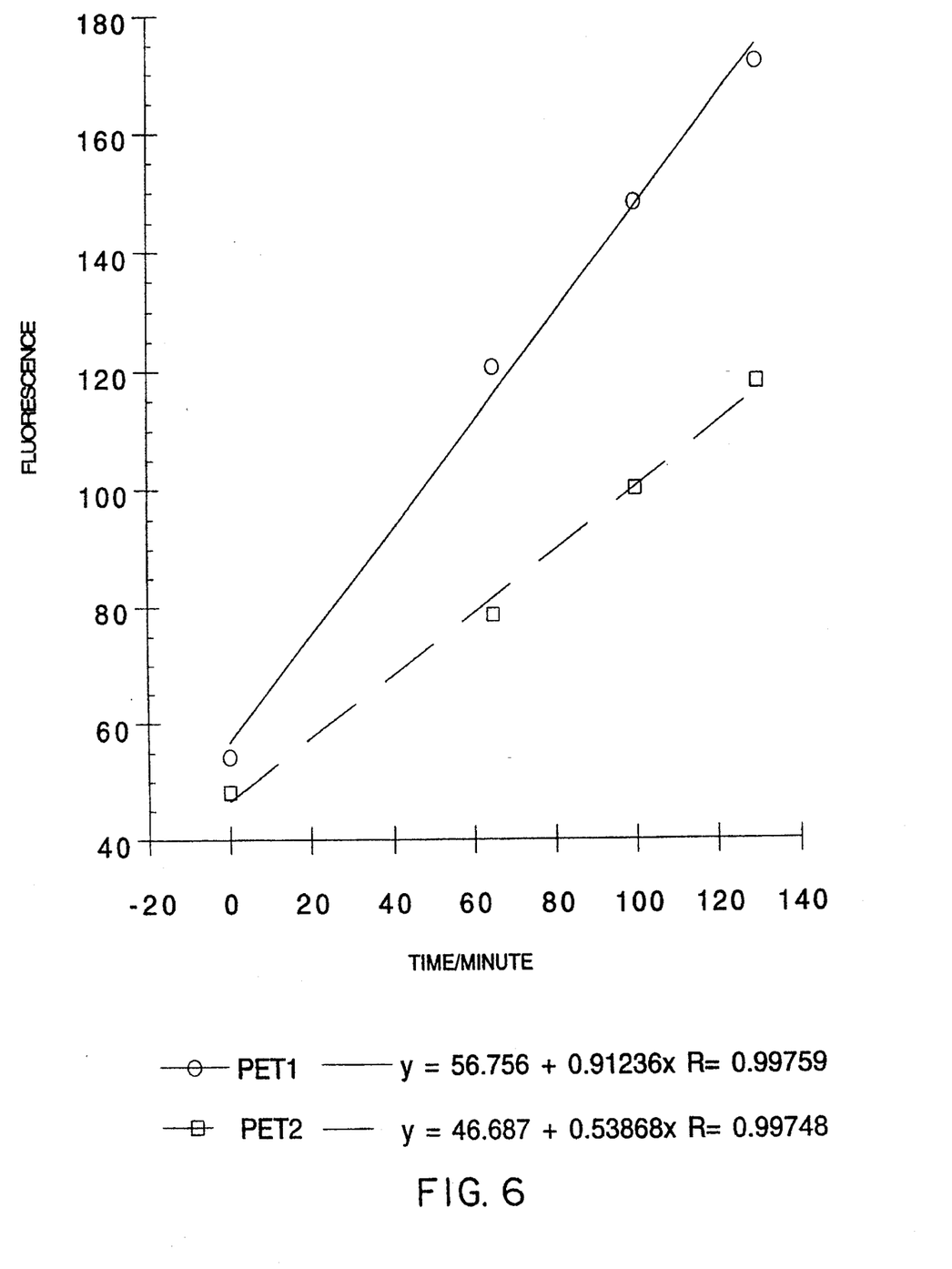
FIG. 6 is a graph comparing the spatially averaged rate of fluorescence of a 1 mil and 2 mil polyester film samples analyzed using the present invention.
Figure 7:
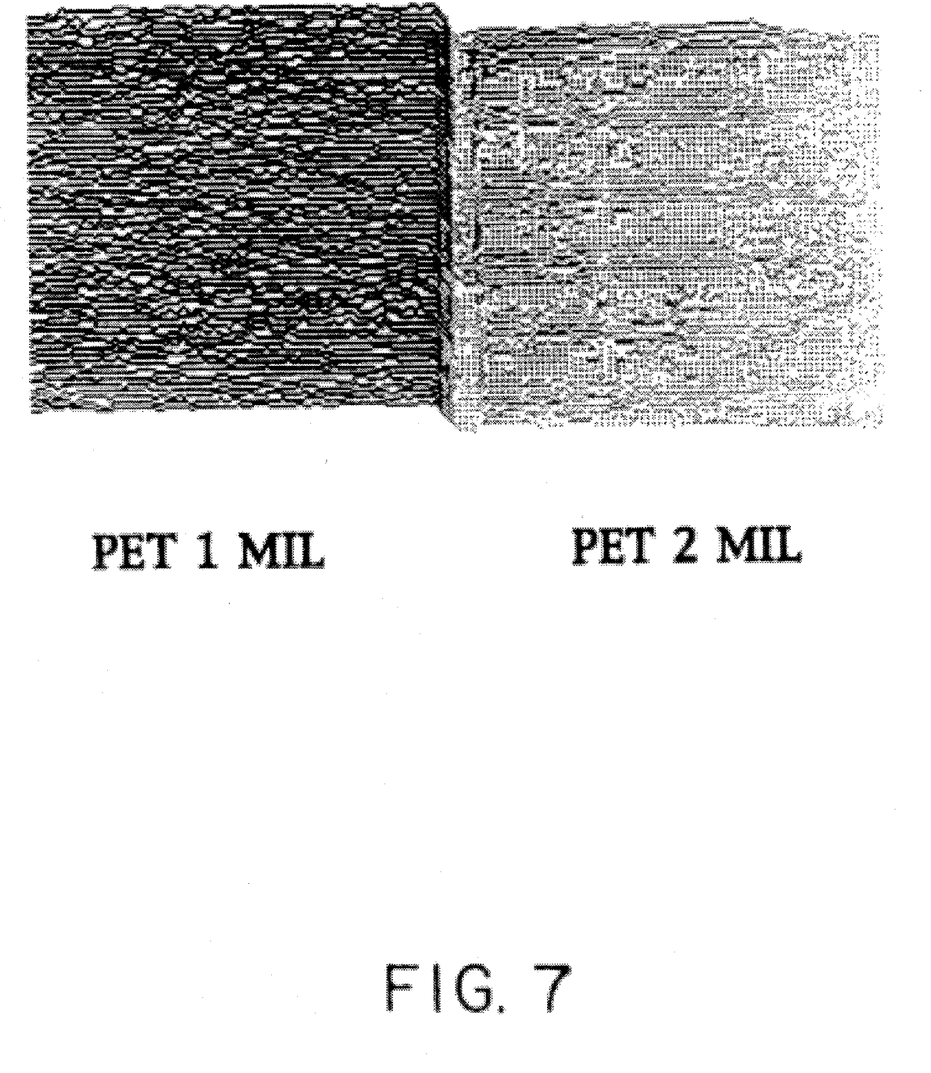
FIG. 7 shows the permeation pattern of the same samples as images.
Figure 8:
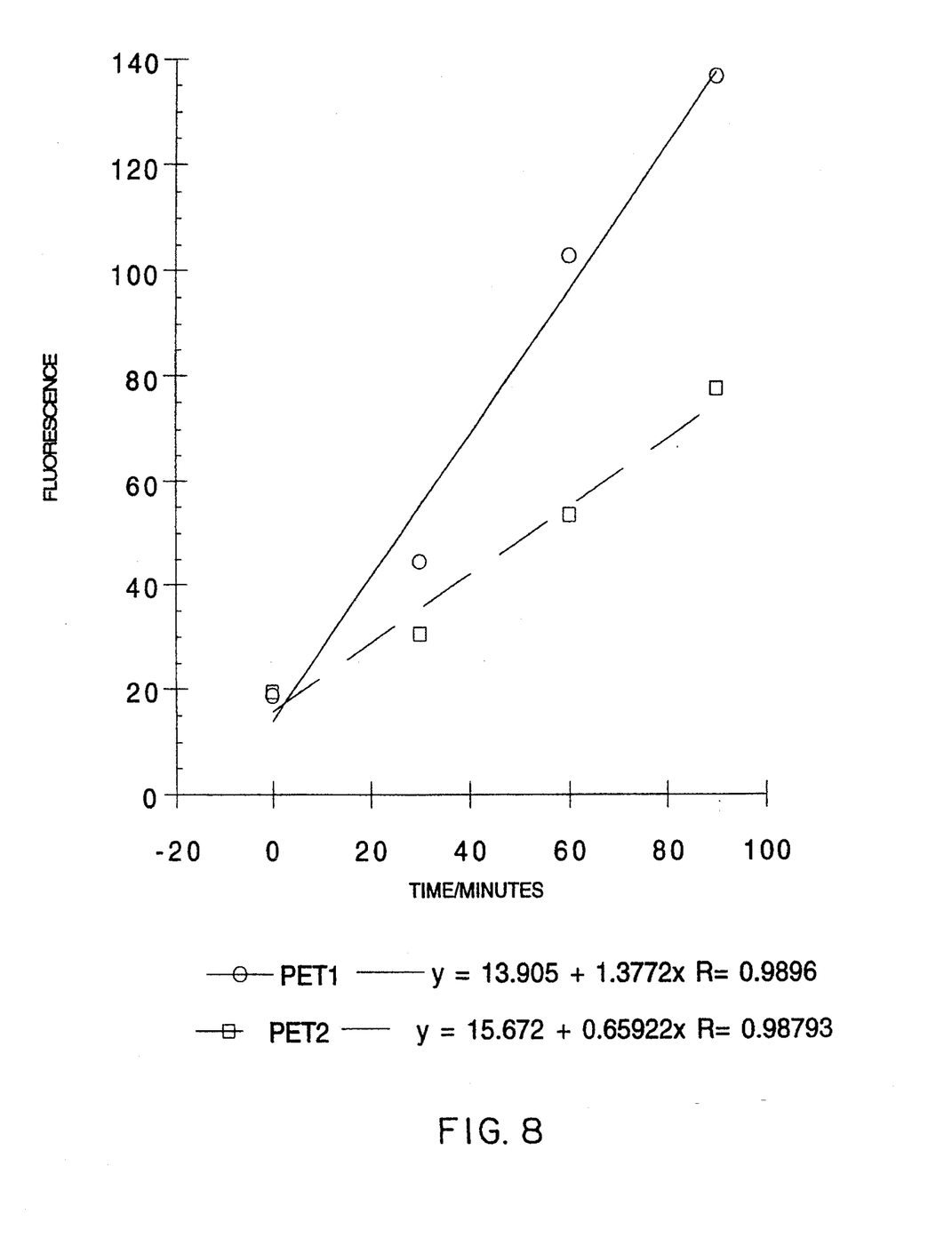
FIG. 8 is a graph comparing the spatially averaged rate of fluorescence of a 1 mil and 2 mil polyester film obtained by a similar fluorescent method without using the present invention.

FIG. 6 shows the change in fluorescence with time when the peelable bag is used. The same results are shown as spatially resolved images in FIG. 7. FIG. 8 shows that similar results are obtained without using the peelable bag, i.e., the samples were vacuum bagged and then the bags completely removed. When these test results are normalized, the results are essentially the same.

THE SUPPORT

The support lends physical stability to the sample for the purposes of the permeability analysis, and preferably is also a very high oxygen barrier and has a sealable surface. It is often desirable that the support be transparent so that the indicator can be photoreduced and also a fluorescence reading can be taken through it. This is particularly true when the test article is opaque or would otherwise interfere with the reading of the fluorescence changes. The support could easily be made as rigid as a glass plate, but might be as flexible as a roll of photographic film. The physical handling characteristics of the support may be determined by the demands of the machinery used to automate the gas permeability analysis. One of ordinary skill in the art will readily recognize that a broad variety of support structures and physical characteristics are readily available.

The support may be a single material, but may also be conveniently constructed as a multilayer structure. For example, the support structure may comprise one or more constituent layers designed to contribute physical stability, gas barrier, clarity, and sealability, to the support.

If the support is a multilayer film, the layer which is chiefly responsible for providing physical stability can be a flat sheet of thermoplastic material. Any of the poly(vinylidene)chloride copolymers can be used, including those based on vinyl chloride, methyl acrylate, and acrylonitrile. Some of these materials are extrudable and also exhibit very good gas barrier characteristics as well as good physical stability. Such materials are commercially available under the tradename Saran™ from Dow Chemical Company, Midland, Mich. Other materials are useable, such as polyesters, metallic foils, polystyrene foam, and cellulosic nonwovens such as paper or cardboard.

The constituent gas barrier layer or layers in this instance must yield an effective gas barrier. That is, a gas barrier high enough so that the support does not become a source of gas contamination for the sample of the material being tested. This can be accomplished in any number of ways, including using the simple expedient of providing either more gas barrier layers or a significantly thicker gas barrier layer in the support structure than the test article has. Typical "gas barriers", are layers of material having a gas transmission rate equal to or less than 500 cubic centimeters per square meter per day per atmosphere ($cc/m^2 \cdot day \cdot atm$) at room temperature, i.e. about 25° C. Polymeric oxygen barrier layers of 40 $cc/m^2 \cdot day \cdot atm$ or less are well known.

Typical materials useful for making oxygen barrier layers are poly(ethylene vinyl alcohol) ("EVOH"), polyacrylonitrile, polyvinyl chloride, poly(vinylidene dichloride), polyethylene terephthalate, silica, and polyamides. "EVOH" as used herein is an ethylene vinyl alcohol copolymer having an ethylene content of preferably 32%. Commercially available resins include EVAL EC-F101(EVALCA), Nippon Goshei Soarnol D, DT, and ZL, and Solvay Clarene R. Ethylene content for the EVOH is preferably between about 20% and 40%, and more preferably between about 25% and 35%. An ethylene content of about 32% by weight is most preferred. The copolymer is alternatively referred to as a hydrolyzed or saponified ethylene vinyl acetate copolymer. Preferably the saponification is carried out to a high degree, that is, greater than 90%.

The polyvinylchloride ("PVC") and poly(vinylidene dichloride) ("PVDC") materials include normally crystalline polymers, both homopolymers and copolymers, containing vinylidene chloride. As copolymerizable materials there can be used vinyl chloride, acrylonitrile, vinyl acetate, ethyl acrylate, ethyl methacrylate and methyl methacrylate. Terpolymers can also be employed, e.g. a terpolymer of vinylidene chloride, dimethyl maleate and vinyl chloride. In general, the vinylidene chloride constituent is at least 50 percent of the material in the polymer, and preferably in the range of 60 to 80 percent, and is a blend of 5–40% suspension polymer and 60–95% emulsion polymer, preferably with an epoxy resin blended therewith in an amount of 2–10%.

An alternate barrier layer can be formed from a latex emulsion coating grade of vinylidene chloride/vinyl chloride having 5–15% vinyl chloride. In a preferred form the coating grade polymer of vinylidene chloride/vinyl chloride is present in an amount of from 5–100% (of total solids) with the remainder being 2–10% epoxy resin and melt extrusion grade material.

The term "polyamide" refers to high molecular weight polymers having amide linkages along the molecular chain, and refers more specifically to synthetic polyamide such as various Nylons such as Nylon 6, 66, 6/12 6/66 and 6/69, including high density versions and nylon copolymers.

Copolymers of certain materials described above, and metal foil or silica layers, can also be employed.

The support structure is also preferably sealable. Sealability is often provided by way of a sealant layer. In this case, the support will be sealed to a peelable film, and so a sealable layer will be present on the support, the peelable film, or both. The sealable layer is preferably a heat sealable layer capable of sealing to a polymeric surface with a bond strength greater than the force required to rupture and subsequently delaminate the permeable layer from the impermeable layer. Other methods of sealing are known to the art including but not limited to adhesive bonding, mechanical clamping, and corona lamination.

The sealant layer can be a crosslinkable polyolefin or a homopolymer, copolymer, terpolymer or graft copolymer of an alpha olefin such as propylene, ethylene and 1-butene. For example copolymers of ethylene and propylene having an ethylene content of 3–10% by weight (EPC) are heat sealable. Also, ethylene vinylacetate (EVA) having a vinyl acetate/ethylene weight ratio of 5–20%, preferably 8–12%, may be mentioned. Other useful materials are low density (branched) polyethylene ("LDPE") where the density is about 0.915–0.925, linear low density polyethylene ("LLDPE") where the density is in the range of 0.920 to 0.924, very low density polyethylene ("VLDPE"), having density below 0.910. Acrylate polymers such as ethylene (meth)acrylic acid "EMAA", ethylene acrylic acid "EAA" as well as ethylene n-butyl acrylate "EnBA", as well as the metal salts of (meth)acrylic acid copolymers ("Ionomers"), may also be used. In addition, this layer commonly includes antiblock and antifog additives.

A useful subclass of sealant layers are self-weldable layers. These layers will self-weld under mild heat, and are preferably ethylene vinyl acetate copolymers, and more preferably Ionomers and an EVA with about 10–14% vinyl acetate comonomer and acrylate copolymers.

Various materials contribute toughness or overall durability to a film structure. These materials often have multiple uses or functions in a film structure. These include ethylene propylene copolymers, various polyethylenes, and Ionomers discussed above, with respect to sealant layers.

MULTILAYER PEELABLE BARRIER

The multilayer peelable barrier is a thermoplastic film which is preferably a coextruded film that has a weakly bonded interface between two layers. Pairs of materials which do not adhere readily to one another include ethylene vinyl alcohol (EVOH) with very low density polyethylene (LDPE). A linear ethylene/alpha-olefin copolymer having a density of about 0.900 to 0.940 g/cc is preferred.

In addition to having a layer made of one of the pair of slightly adhering materials, the relatively impermeable portion of the multilayer peelable barrier typically includes one or more of the same type of gas barrier layers which can be used in the support. Any number of other layers adding other qualities, such as resistance to abuse, good optical qualities and improved adhesion between layers which are not intended to be separable, may also be included.

In addition to having a layer made of one of the pair of slightly adhering materials, the relatively permeable portion of the multilayer peelable barrier typically includes a sealant layer to ensure good adhesion to the support. This sealant layer may be any of the sealant materials which would be useful for the support, as described above. The self-weldable materials are often favored, as their adhesion is particularly effective, and considerably exceeds the bond strength between the weakly adhered layers.

The permeable layer typically includes a number of other layers imparting desirable properties such as strength, resistance to abuse, good adhesion between layers, and good optical properties. These are much the same materials which may be used in either the support or impermeable multilayer structures, provided that the ultimate gas barrier is not high enough to interfere with the gas permeability analysis. For analysis of the oxygen transmission rates, the oxygen permeable layer preferably has an oxygen transmission rate of at least about 1,000, preferably about 5,000 cc/m$^2$.atm.day. As used in the present invention, the permeable layer affects the absolute rate of increase of fluorescence. A less permeable layer will cause the fluorescence to increase slightly more slowly. Since each sample is run against a control, the results are normalized, and found to correlate with tests run without using the peelable film.

The support layer is typically transparent, and both photoreduction and fluorescence readings can be taken from the support side. However, if the support layer is not transparent, fluorescence readings can be taken through a transparent permeable layer.

The following example illustrates the use of the invention described herein without limiting its scope or the scope of the claims which follow.

EXAMPLE 1

A gel was made incorporating an oxidation-reduction system with riboflavin as the oxidizable substrate and sodium EDTA as a reducing aid during the photo-reduction process. The recipe for the gel was as follows:

| | |
|---|---|
| Gelatin | 7 grams/100 mls water |
| Disodium EDTA | 300 milligrams/100 mls water |
| Riboflavin | 20 milligrams/100 mls water |
| Antifoam B | 1 drop (to prevent foaming of solution) |

The gel was impregnated onto non-fluorescent Whatman CMM CHR chromatography paper cut to a convenient size to make indicator strips.

Samples of polyester film 1 mil and 2 mil thick (Mylar™ from E. I. DuPont de Nemours & Co., Wilmington, Del.) were vacuum packaged in between a support layer of poly(vinylidine dichloride) coated polyvinyl chloride film with ethylene vinyl acetate sealant (V095BN film available from the Cryovac Division of W. R. Grace & Co.-Conn., Duncan, S.C.) and a peelable gas barrier film (LDX 3690, available from Cryovac). The samples were stored overnight. When the time came to analyze the samples, the impermeable layer was peeled away to expose the test films to oxygen in the dark at ambient temperature. The rate of fluorescence of the films is shown in FIG. 6. The rate of fluorescence of the 1 and 2 mil materials was analyzed to be 0.912 and 0.558 respectively. This indicates that the rate of oxygen transmission for the 1 mil film was approximately double that of the 2 mil film. The rate of oxygen transmission for these materials as measured by the standard method disclosed in U.S. Pat. No. 5,107,696 is 68 and 34 cc/m$^2$.day.atm at 21° C., respectively. FIG. 7 shows the permeation pattern obtained. The color patterns of the two images are very uniform, which is typical of these materials. Once these samples are normalized for controls, there is essentially no difference between the test results obtained using the peelable barrier package and the same test run without using a bag, or where a sample is vacuum bagged and the vacuum bag is then entirely removed. FIG. 8 shows the fluorescence curves obtained using a vacuum bag that did not have a peelable barrier layer. The vacuum bag was removed shortly before the fluorescence analysis was begun.

It is more convenient to use the peelable vacuum bags, as the samples can be stored in reduced form for an extended amount of time before the test is actually run. With unbagged samples, fluorescence changes begin almost immediately and the experimental error is higher. With non-peelable bags, some sort of support must normally be packaged with the indicator and test object, and the test object must be sealed to the support. Samples can come apart when the non-peelable bags are removed.

What is claimed is:

1. In a method for detecting the permeability of an object to a gas, the improvement comprising vacuum packaging an indicator and a test object in a device comprising
   a. a support having an effective barrier to the gas, and
   b. a multilayer film having a gas barrier portion that is peelable from a permeable portion, the permeable portion being sealed to the support.

2. The method of claim 1, wherein the support comprises a constituent layer selected from the group consisting of extrudable thermoplastics, polystyrene foam or nonwoven cellulosic materials, and a gas barrier coating or layer.

3. The method of claim 2, wherein the gas barrier coating or layer is selected from the group consisting of poly (ethylene vinyl alcohol), metallic foil, polyacrylonitrile, polyvinyl chloride, poly(vinylidene dichloride), polyethylene terephthalate, silica, and polyamide.

4. The method of claim 3, wherein the gas barrier coating or layer is poly (ethylene vinyl alcohol) and the support further comprises one or more layers comprising a metal salt of a (meth)acrylic acid copolymer.

5. The method of claim 1, wherein the support further comprises a sealant coating or layer.

6. The method of claim 5, wherein the sealant coating or layer is a polymeric material selected from the group consisting of ethylene alpha olefin copolymer, ethylene vinyl acetate copolymer, ethylene methyl acrylate copolymer, a metal salt of a (meth)acrylic acid copolymer and mixtures thereof.

7. The method of claim 1 wherein the gas is oxygen, and the indicator is redox indicator, and wherein the support or the multilayer film, or both, are sufficiently transparent to allow photoreduction, and the support or the permeable portion of the multilayer film, or both, are sufficiently transparent to allow visualization of indicator changes.

8. The method of claim 7, wherein the gas barrier layer comprises poly (ethylene vinyl alcohol) and the gas impermeable portion further comprises one or more layers comprising a metal salt of a (meth)acrylic acid copolymer.

9. The method of claim 1, wherein the multilayer, film is separable into a permeable portion and gas barrier portion, the permeable portion having a plurality of layers including:
   (1) a heat sealable layer which is a polymeric material selected from the group consisting of ethylene alpha olefin copolymer, ethylene vinyl acetate copolymer, ethylene methyl acrylate copolymer, and mixtures thereof, and
   (2) a layer comprising a linear ethylene/alpha-olefin copolymer; and the gas barrier portion having a plurality of layers including
   (3) a gas barrier layer comprising a material selected from the group consisting of poly (ethylene vinyl alcohol), polyacrylonitrile, polyvinyl chloride, poly(vinylidene dichloride), polyethylene terephthalate, silica, and polyamide; and,
   (4) an outer or second surface layer of polymeric material; and
   wherein the heat sealable layer (1) is capable of sealing to a polymeric surface with a bond strength greater than the force required to rupture and subsequently delaminate the permeable layer from the impermeable layer.

10. A device comprising
   a. a sealable support having an effective barrier to a gas;
   b. a multilayer film having a gas barrier portion that is peelable from a permeable portion, the permeable portion being sealable to the support; and
   c. a gas indicator adjacent to the support,
   wherein the support and the gas barrier portion are in a sealing relationship.

11. The device of claim 10, wherein the multilayer, film is separable into a permeable portion and gas barrier portion, the permeable portion having a plurality of layers including:
   (1) a heat sealable layer which is a polymeric material selected from the group consisting of ethylene alpha olefin copolymer, ethylene vinyl acetate copolymer, ethylene methyl acrylate copolymer, and mixtures thereof, and (2) a layer comprising a linear ethylene/alpha-olefin copolymer; and the gas barrier portion having a plurality of layers including (3) a gas barrier layer comprising a material selected from the group consisting of poly (ethylene vinyl alcohol), polyacrylonitrile, polyvinyl chloride, poly(vinylidene dichloride), polyethylene terephthalate, silica, and polyamide; and, (4) an outer or second surface layer of polymeric material; and wherein the heat sealable layer (1) is capable of sealing to a polymeric surface with a bond strength greater than the force required to rupture and subsequently delaminate the permeable layer from the impermeable layer.

12. The device of claim 11, wherein the gas barrier layer comprises poly (ethylene vinyl alcohol) and the gas impermeable film further comprises one or more layers comprising a metal salt of a (meth)acrylic acid copolymer.

13. The device of claim 11, wherein the indicator is a redox indicator.

14. The device of claim 13 wherein the redox indicator is selected from the group consisting of thiazine derivatives, oxazine derivatives, flavin, or mixtures thereof.

15. The device of claim 10, 11, 12, 13 or 14 further comprising a test article adjacent to the gas indicator and the multilayer film.

* * * * *